United States Patent [19]

Dorman et al.

[11] Patent Number: 4,661,536

[45] Date of Patent: Apr. 28, 1987

[54] PROCESS FOR THE PREPARATION OF HARD TISSUE PROSTHETICS

[75] Inventors: Linneaus C. Dorman, Midland, Mich.; Paul A. Meyers, Dublin, Calif.

[73] Assignee: The Dow Chemical Company, Midland, Mich.

[21] Appl. No.: 914,687

[22] Filed: Oct. 2, 1986

Related U.S. Application Data

[62] Division of Ser. No. 702,999, Feb. 19, 1985, Pat. No. 4,634,720.

[51] Int. Cl.$^4$ ................................................. A61F 2/00
[52] U.S. Cl. ..................................... 523/113; 523/114; 523/115; 524/514; 524/517; 623/16
[58] Field of Search ................. 524/414, 417; 523/113, 523/114, 115; 3/1.9

[56] References Cited

U.S. PATENT DOCUMENTS

| | | | |
|---|---|---|---|
| 3,658,831 | 4/1972 | Fujimoto et al. | 260/307 B |
| 3,787,900 | 1/1974 | McGee | 106/35 |
| 4,192,021 | 3/1980 | Deibig et al. | 106/161 |
| 4,199,864 | 4/1980 | Ashman | 433/175 |
| 4,222,128 | 9/1980 | Tomonaga et al. | 106/35 |
| 4,347,234 | 8/1982 | Wahlig et al. | 424/19 |
| 4,362,842 | 12/1982 | Masuhara et al. | 524/854 |
| 4,373,217 | 2/1983 | Draenert | 523/114 |
| 4,451,235 | 5/1984 | Okuda et al. | 523/115 |
| 4,595,713 | 6/1986 | St. John | 523/114 |

FOREIGN PATENT DOCUMENTS 1593288 7/1981 United Kingdom .

*Primary Examiner*—Morton Foelak

[57] ABSTRACT

An in situ polymerization process is disclosed whereby an α-amino acid N-carboxyanhydride is blended intimately and efficiently with one or more calcium phosphate biomaterials. The polymerization proceeds at ambient temperature and pressure without the need for initiators or surface modification of the calcium phosphate biomaterials. The resulting composite material may subsequently be ground and blended with a compatible water soluble pore-forming agent and then molded to form dense, shaped objects which may be made porous by leaching out said water soluble pore-forming agent. The resulting shaped objects may then be used as hard tissue prosthetics either alone or in conjunction with conventional prostheses.

12 Claims, 2 Drawing Figures

PROCESS FOR THE PREPARATION OF HARD TISSUE PROSTHETICS

This is a divisional of application Ser. No. 702,999, filed Feb. 19, 1985 now U.S. Pat. No. 4,634,720.

FIELD OF THE INVENTION

The present invention relates to an in situ polymerization process for the preparation of composite materials comprising an α-amino acid polymer and a calcium phosphate biomaterial. Said composite materials are useful as hard tissue prosthetics such as bone prosthetics.

BACKGROUND OF THE INVENTION

Calcium phosphates are known in the art as physiologically acceptable biomaterials potentially useful as hard tissue prosthetics. The most widely studied of these are hydroxyapatite and tricalcium phosphate. When these materials are shaped and made porous they can be used alone or as a supplement or extender with bone for hard tissue prosthetics. Under appropriate conditions and with an appropriate form of calcium phosphate, the calcium phosphate is resorbed and new bone growth results. Calcium phosphate biomaterials can be molded by compaction under high pressure. Pore formation of molded calcium phosphate biomaterials is generally achieved by compaction of calcium phosphate powders containing naphthalene followed by removal of the naphthalene by leaching or sublimation. Hydrothermal exchange of marine coral structures (i.e., calcium carbonate for calcium phosphate), and decomposition of hydrogen peroxide have also been employed to generate pore filled structures.

The dense or "green" forms of the calcium phosphate implant materials have mechanical properties equal to or exceeding that of natural bone, but their respective porous forms do not, thus severely limiting their usefulness as hard tissue prosthetics.

The art teaches that natural and synthetic polymers can be used in conjunction with various inorganic mineral fillers such as porous and powdered forms of calcium phosphate to enhance their mechanical properties for use as hard tissue prosthetics or to enhance the bonding of metallic or plastic prosthetics to natural tissue. Natural polymers include collagen (U.S. Pat. No. 4,192,021) and gelatin (German Pat. No. 2,812,696). Synthetic polymers include polyacrylates, poly(methylmethacrylate), polyethylene, polysulfones, polyamides, polyesters, polytetrafluoroethylene, and polycarbonates (Great Britain patent application Ser. No. 2,031,450A); polyacetates and polyglycolates (U.S. Pat. No. 4,192,021); epoxides, polyacrylamide, polypropylene, polyurethanes, polyacetals, silicone resins, and furan resins (U.S. Pat. No. 4,222,128); polyvinyl pyrrolidone, polyvinyl alcohol (U.S. Pat. No. 4,263,185); and a crosslinked pentapeptide (U.S. Pat. No. 4,187,852). The natural polymers and some of the synthetic polymers are resorbable, i.e., biodegradable.

The art also teaches that nontoxic water soluble substances such as sodium chloride can be incorporated into a mixture of powdered acrylic polymer, liquid monomer, and other ingredients in a mold and the mixture polymerized to produce a shaped composite. The composite can then be made porous by leaching the sodium chloride with water (U.S. Pat. No. 4,199,864).

The various polymer-calcium phosphate composites are prepared in a number of ways including blending calcium phosphates with polymeric binder and subsequent molding (Great Britain Pat. No. 1,593,288); impregnation of sintered, porous calcium phosphate with polymers under vacuum (Great Britain Pat. No. 1,593,288); impregnation of a porous calcium phosphate body with the melt or solution of prepolymers and solidifying the polymers by further polymerization or curing in the pores or by evaporation of the solvent (U.S. Pat. No. 4,192,021); impregnation of a porous calcium phosphate body with a very reactive monomer like an α-cyanoacrylate or monomer and catalyst and polymerizing by heating (U.S. Pat. No. 4,192,021); compression molding of an intimately blended, finely powdered mixture of polymer and calcium phosphate (U.S. Pat. No. 4,192,021); and embedding ceramic calcium phosphate particles into resins where the calcium phosphate particles have previously been coated with a resin-affinic material to ensure good bonding to the resin, or copolymerizing precoated particles with the resin monomers (German Pat. No. 2,620,907).

Calcium phosphate-polymer composite materials can also be used in conjunction with metallic or plastic prosthetics to facilitate adhesion and bone growth around the prosthetic (German Pat. No. 2,905,647). The composite can also be applied as a coating, for example, to an anodized titanium/aluminum/vanadium alloy hip prosthetic (Great Britain Pat. No. 1,593,288). The essential element in anchoring prosthetic devices appears to be the induction of new bone growth around the device by assuring that contact with the surrounding tissue is through a sheath of, or a surface laden with, bioactive calcium phosphate.

SUMMARY OF THE INVENTION

The present invention is directed to a process for preparing composite materials of an α-amino acid polymer and a calcium phosphate biomaterial by the in situ polymerization of the corresponding reactive monomer of the α-amino acid (i.e., the α-amino acid N-carboxyanhydride) and the calcium phosphate biomaterial when the two components are admixed in a suitable solvent vehicle. The composite materials prepared by the in situ process of the present invention can subsequently be blended with a compatible, pore-forming agent such as a water soluble polymer or water soluble inert material and then molded to form dense, shaped objects which can be made porous by leaching out said pore-forming agent.

The composite materials disclosed herein may be used in a variety of applications such as, for example, hard tissue prosthetics for dental or orthopedic appliances or other applications where one skilled in the art would envision the use of physiologically acceptable and/or resorbable materials such as those described herein.

DETAILED DESCRIPTION OF THE INVENTION

Figure 1:
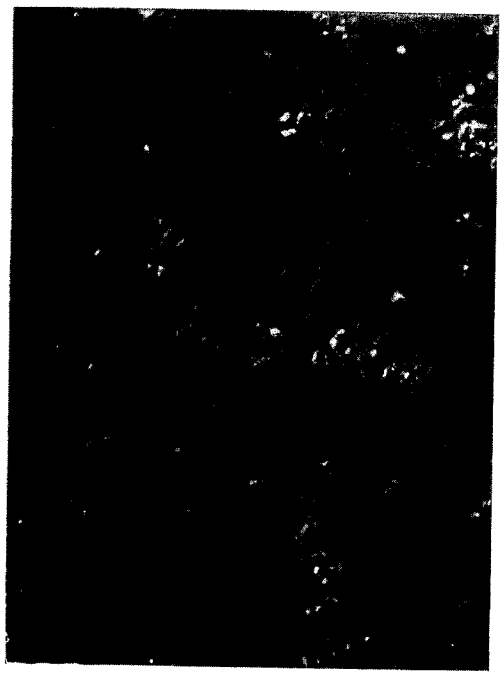
FIG. 1 - Differential interference contrast photomicrograph of unsintered hydroxyapatite, 500X.

The α-amino acids used in the process of the present invention may be any of the common, naturally occurring or synthetic α-amino acids capable of undergoing polymerization through the corresponding reactive α-amino acid N-carboxyanhydride monomer (for convenience, hereinafter referred to as α-amino acid NCA).

Examples of the α-amino acids which may be used include compounds such as aspartic acid, glutamic acid, lysine, arginine, alanine, valine, leucine, serine and the like. The α-amino acids used herein may be present in the D or L configuration or in the D,L configuration.

It is necessary to insure that during the α-amino acid NCA polymerization no side chain reactions or interactions between amino and carboxyl functions of different amino acids occur. Such situations may be prevented by carrying out the reaction in such a way as to avoid said interactions or by using α-amino acids wherein protecting groups have been added to the side chain, amino and/or carboxyl functions. Amino acids having such protected functionalities are readily prepared by known techniques or are commercially available. See for example, the following publications: *Solid Phase Peptide Synthesis*, J. Stewart and J. Young, W. H. Freeman & Co., San Francisco, 1969; *Synthetic Peptides*, G. Pettit, Vol. 1 (1970) and Vol. 2 (1971), Von Nostrand Reinhold Co., New York; and *The Peptides, Analysis, Synthesis, Biology*, E. Gross and J. Meienhofer, Academic Press, New York, 1979.

Of the α-amino acids which may be used in the present invention, glutamic acid is preferred. Glutamic acid may be polymerized by known techniques without the addition of the above-described protecting groups, or derivatives of glutamic acid may be used. Especially preferred for use herein are the γ-ester derivatives of glutamic acid of the formula:

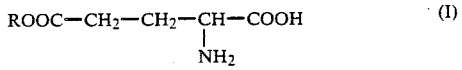

wherein R represents alkyl or aralkyl. As used herein, the term "alkyl" refers to aliphatic, straight or branched chain radicals of from about 1 to about 10 carbon atoms or cyclic aliphatic radicals of from about 3 to about 8 carbon atoms; "aralkyl" refers to radicals such as, for example, phenylethyl, benzyl, ring-substituted benzyl and the like. Most particularly preferred for use herein are those compounds of formula I wherein R is methyl or benzyl.

The α-amino acid NCA referred to above is prepared by the reaction of the desired α-amino acid with phosgene via procedures known to the art. See, for example, U.S. Pat. No. 3,658,831, and Fuller et al., "A Procedure for the Facile Synthesis of Amino-Acid N-Carboxyanhydrides" (*Biopolymers*, Vol. 15, p. 1869, 1976) which are incorporated herein by reference. For purposes of illustration, the N-carboxyanhydride of a compound of formula I is prepared by the following reaction sequence (where R is as defined for formula I):

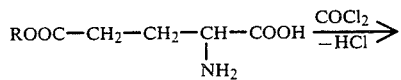

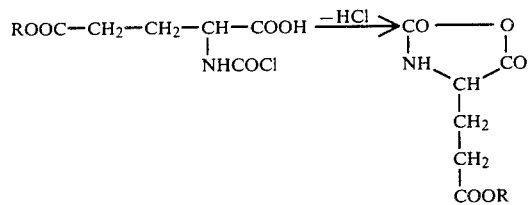

The α-amino acid NCA is then readily polymerized into the α-amino acid polymer as represented by the following:

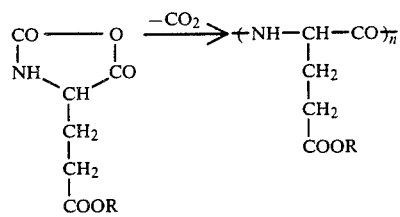

wherein R is as defined for Formula I and n is a positive integer. The other α-amino acid polymers alluded to herein may be prepared in a manner analogous to the above-described reactions; the use of compounds of Formula I is merely illustrative.

In the process of the present invention, the α-amino acid NCA is polymerized in the presence of one or more calcium phosphate biomaterials. The calcium phosphate biomaterial may be one or more of the compounds disclosed by M. Jarcho in "Calcium Phosphate Ceramics as Hard Tissue Prosthetics" published in *Clinical Orthopaedics*, June, Vol. 157, J. B. Lippincott Co., 1981 such as, for example, sintered or unsintered calcium phosphate tribasic ($Ca_{10}(OH)_2(PO_4)_6$) also known as hydroxyapatite, or simply apatite, tricalcium phosphate ($Ca_3(PO_4)_2$), or various calcium pyrophosphates. The composite materials thus formed may contain from about 25 to about 75 percent by weight, preferably from about 40 to about 60 percent by weight, of one or more calcium phosphate biomaterials, said biomaterials preferably being hydroxyapatite, tricalcium phosphate or mixtures thereof.

Optionally, and preferably, the composite material prepared by the in situ polymerization process may subsequently be made porous in order to facilitate tissue ingrowth, a phenomenon where tissue such as bone and tendon continue to grow after the prosthetic device is in place and occupy apertures adjacent to the tissue. The tissue ingrowth provides a means by which a prosthetic device may be secured, thereby providing mechanical stabilization of the implant.

The composites prepared as described herein are permeable to oxygen and water and are biodegradable, presumably due to the presence of peptide bonds in the α-amino acid polymer matrix making the substances protein-like. As resorption of the calcium phosphate biomaterial occurs followed by a slow degradation of the α-amino acid polymer matrix, further porositization results, thereby facilitating tissue ingrowth. For example, as the calcium phosphate biomaterial is resorbed and the α-amino acid polymer matrix slowly degrades, new, natural, self-supporting hard tissue develops.

Further, various combinations of α-amino acids may be polymerized with one or more calcium phosphate biomaterials. By so doing, the characteristics of the resulting composite material may be modified so as to vary the rate of resorption of the inorganic filler and/or the rate of degradation of the polymer matrix, thus allowing one skilled in the art to design a given composite for a highly specific application.

The composite materials prepared by the in situ process of the present invention may be ground to fine, free-flowing powders making them convenient to use. The free-flowing powders can be readily molded to virtually any shape, preferably a shape capable of anatomical use as a prosthetic device. Such anatomically-shaped forms may then be surgically implanted into animals in need of such prostheses thereby providing supplementation or replacement of hard tissue. It is further contemplated that the composite materials described herein may be used in conjunction with conventional prosthetic devices known to the art. (See, for example, publications such as U.S. Pat. Nos. 4,362,681, 4,351,069 and 3,986,212, which describe various conventional prostheses.) For instance, in total hip joint replacements, it would be possible to mold one or more of the composite materials prepared by the process of the present invention about the metal stem of the prosthetic which, when implanted into the femur, would present a compatible surface for new bone growth while being sufficiently strong to support the metal prosthesis. This and other applications of the technology disclosed herein will be readily appreciated by one skilled in the art.

In preparing the reactive $\alpha$-amino acid NCA monomer used in the in situ process of the present invention, the desired $\alpha$-amino acid (having, if necessary, protected side chain, amino and/or carboxyl functionalities) is treated with phosgene. While various phosgenation processes are known to the art, it is preferable that a process substantially the same as that described in U.S. Pat. No. 3,658,831 be utilized in order to prepare an $\alpha$-amino acid NCA of the desired purity. It is important to obtain very highly pure $\alpha$-amino acid NCA in order to prepare $\alpha$-amino acid polymers having a high degree of polymerization and high quality.

The $\alpha$-amino acid NCA thus obtained is then admixed with one or more of the desired calcium phosphate biomaterials in a suitable inert organic solvent such as chloroform, dioxane, tetrahydrofuran (THF), methylene chloride or mixtures thereof. Preferably, the inert organic solvent utilized is dioxane, THF or mixtures thereof. The calcium phosphate biomaterial must be in a powdered or particulate form. Typically the calcium phosphate particles are between about 0.05 micrometers ($\mu$m) and about 10 $\mu$m in diameter and preferably about 1 $\mu$m in diameter. As noted earlier, the composite material may be composed of from about 25 to about 75 percent by weight, preferably from about 40 to about 60 percent by weight of one or more calcium phosphate biomaterials, preferably hydroxyapatite, tricalcium phosphate, or mixtures thereof. Correspondingly, the $\alpha$-amino acid polymer represents from about 75 to about 25 percent by weight, preferably from about 60 to about 40 percent by weight of the composite formed. Typically, the $\alpha$-amino acid NCA and calcium phosphate biomaterial mixture is stirred for a period of time sufficient to effect formation of the desired composite material (usually from about 2 to about 12 days) at a temperature of from about 18° to about 30° C. It is preferred that the mixture be stirred for about 3 to about 6 days at ambient temperature and pressure.

The above-desribed in situ process of the present invention is a significant improvement over the processes taught in the prior art. The in situ process of the present invention does not require exogenous catalysts or initiators for polymerization of the $\alpha$-amino acid NCA. The polymerization of the $\alpha$-amino acid NCA is catalyzed by the surfaces of the calcium phosphate particles. Further, the surfaces of the calcium phosphate particles do not require the presence of resins or other coupling agents. The calcium phosphate particles do not have to be surface modified prior to the in situ polymerization of the $\alpha$-amino acid NCA. In addition, the in situ polymerization process of the present invention proceeds spontaneously at ambient temperature without the need for heating or cooling. Also, it is unnecessary to use a solvent system in which both the $\alpha$-amino acid NCA monomer and resultant $\alpha$-amino acid polymer are soluble. For example, poly($\gamma$-methyl)-L-glutamate is insoluble in dioxane or THF, two solvents frequently used for the polymerization. The in situ process of the present invention is less complicated, is less costly, and requires fewer steps than the prior art processes.

Figure 2:
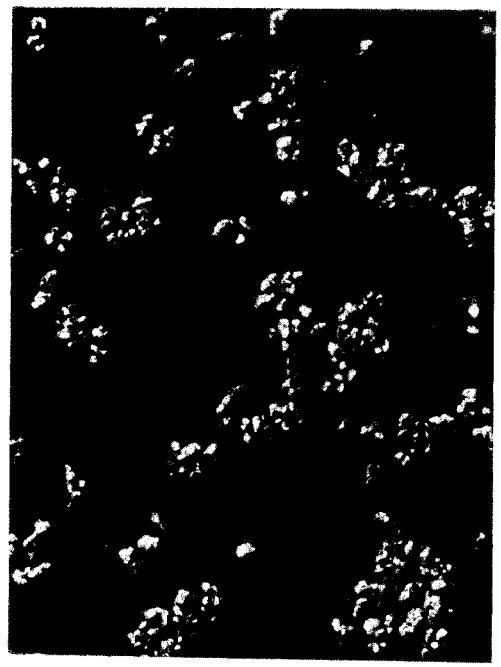
FIG. 2 - Differential interference contrast photomicrograph of a composite of unsintered hydroxyapatite and in situ formed poly(γ-methyl L-glutamate), 50 weight percent hydroxyapatite, 500X.

In addition to the hereinabove described advantages, the in situ process of the present invention results in an intimate bonding between the resulting $\alpha$-amino acid polymer and calcium phosphate biomaterial, not merely a mixture of said components. This intimate bonding is not achieved in more complicated processes employing exogenous catalysts or processes which require surface modification of the calcium phosphate particles. The in situ polymerization process results in maximum contact between the polymer and calcium phosphate. The polymer is in a continuous phase which coats the calcium phosphate particles; this results in relatively constant and uniform dispersion of the calcium phosphate particles in the polymer matrix. The intimate bonding between the polymer and the calcium phosphate biomaterial is illustrated in FIG. 2.

FIG. 1 is a photomicrograph of particles of unsintered hydroxyapatite. FIG. 2 is a photomicrograph, at the same magnification as FIG. 1, of a composite of unsintered hydroxyapatite and poly($\gamma$-methyl L-glutamate) formed by the in situ process which clearly demonstrates the coating of individual hydroxyapatite particles by the $\alpha$-amino acid polymer.

Once the composite material has been prepared it can be molded by techniques well-known to the art to virtually any desired shape while maintaining the complete integrity of the composite material.

Porositization of the composite materials described herein may be attained by intimately blending the powdered composite formed by the in situ process with a compatible, pore-forming agent. Such pore-forming agents include water-soluble polymers (such as poly(2-ethyl-2-oxazoline), hereinafter referred to as PEOX; polyvinyl pyrrolidone; polyvinyl alcohol; or methylcellulose) and/or water-soluble inert materials (such as sodium chloride or potassium chloride). The mixture obtained may then be molded to the desired configuration, followed by a leaching of the compatible, pore-forming agent with water. Said leaching typically occurs satisfactorily in a time from about 2 to about 21 days. Preferably, for the porositization process, PEOX or sodium chloride is utilized as the pore-forming agent in a range of from about 5 to about 30 percent by weight, preferably in a range of from about 10 to about 20 percent by weight (based on the total weight of the composite plus pore-forming agent). Sodium chloride is particularly preferred as a pore-forming agent and is most particularly preferred when used in a range of from about 10 to about 20 percent by weight (based on the total weight of the composite plus pore-forming agent).

The following examples are provided as a means of illustrating the present invention and are not to be construed as a limitation thereon.

EXAMPLE 1

γ-Benzyl L-Glutamate 1416 grams (g) of L-glutamic acid, 1560 g of 60% sulfuric acid and 1152 g of benzyl alcohol were placed in a 12 liter round bottom flask equipped with a distillation head. The mixture was heated to 70° C. and stirred for 45 minutes. Upon cooling, the resulting solution was stirred and was subjected to a reduced pressure. When the vacuum had stabilized at about 100 millimeters (mm) the reaction temperature was again raised to 70° C. and water was distilled off for about 4.5 hours. Upon standing overnight, the reaction mixture became viscous and was slowly added to a stirred mixture of 1613 g of sodium bicarbonate, 1.2 kilograms (kg) of ice and 12 liters of water. A precipitate formed which was collected by filtration and subsequently washed with about 8 liters of carbon dioxide-free water and 8 liters of acetone and subsequently air-dried. The precipitate was triturated with 2 liters of ether and dried, yielding 1044 g of the desired γ-benzyl L-glutamate, melting point (m.p.) 156°–157° C. Thin layer chromatography detected the presence of unreacted glutamic acid in the crude product. The crude product was recrystallized from 12.5 liters of hot water and filtered through a plug of glass wool suspended in the neck of a heated glass funnel. After cooling, and overnight refrigeration, the recrystallized product was collected, and washed with 2 liters of cold water, then 2 liters of THF. The product was air dried overnight and then dried in vacuo at room temperature for three hours. 693 g of γ-benzyl L-glutamate was recovered as white, shiny plates, m.p. 156.5°–157° C.

Following a procedure substantially the same as that described in Example 1, the following two compounds were prepared using the requisite starting materials.

EXAMPLE 2

γ-Benzyl D,L-Glutamate, m.p. 145°–146° C.

EXAMPLE 3

γ-Hexyl L-Glutamate, m.p. 162.5°–163° C.

EXAMPLE 4

γ-Methyl L-Glutamate

A cold solution of 300 ml of acetyl chloride was slowly added to a flask containing 3 liters of methanol. To this mixture was added 442 g of L-glutamic acid. The flask was stoppered and shaken for several minutes to effect solution. The flask was then allowed to stand at room temperature with intermittent shaking for 24 hours. 300 ml of pyridine was added causing a precipitate to form. Upon standing for an additional 48 hours, the precipitate was collected on sintered glass and washed with two 600 ml portions of ethanol and a 250 ml portion of ether. The precipitate was dried in vacuo at room temperature for 3 hours and then in a vacuum desiccator over Drierite ® for 5 hours. Pyridine vapors were still perceptible from the precipitate which was further triturated with ether and dried again yielding 201.5 g of the desired γ-methyl L-glutamate as white, shiny plates, m.p. 168°–169° C.

EXAMPLE 5

γ-Methyl D,L-Glutamate

γ-Methyl D,L-glutamate was prepared by substantially the same method as described in Example 4, yielding white, powder-like crystals, m.p. 166°–166.3° C.

EXAMPLE 6

γ-Benzyl L-Glutamate N-Carboxyanhydride 92.7 g of γ-benzyl L-glutamate and 840 ml of THF were mixed and heated in a 3 liter reaction flask. Nitrogen and phosgene were bubbled in and the reaction temperature was maintained between 45°–50° C. until complete solution of the starting material had occurred (about 2 hours). Heating and phosgene flow were then stopped, but stirring and nitrogen flow were continued as the reaction mixture cooled slowly to 30° C. (approximately 45 minutes). The reaction flask was carefully removed from the phosgenation apparatus and stoppered. The reaction mixture was then concentrated in vacuo to about 250 ml with the aid of a rotary evaporator (maximum bath temperature about 35° C.). The residual concentrate was transferred to a dry flask and diluted carefully with an equal volume of hexane and seeded. After allowing crystallization to proceed at room temperature for about an hour, the reaction mixture was further diluted with about 500 ml of hexane and was maintained at −30° C. for about 8–10 hours. After warming to room temperature the product was collected on a sintered glass funnel, care being taken to minimize contact with atmospheric moisture. The product was rinsed with a mixture of THF-hexane (1:3) and then hexane, covered with a filter paper and dried in a vacuum desiccator over Drierite ®. 92.6 g of the desired γ-benzyl L-glutamate N-carboxyanhydride was recovered as white crystals, m.p. 95°–96° C.

EXAMPLE 7

γ-Methyl L-Glutamate N-Carboxyanhydride 100 g of γ-methyl L-glutamate and 600 ml of THF were placed in a 2 liter flask under nitrogen. The ensuing phosgenation reaction was carried out as described in Example 6, above. The reaction temperature was maintained between 44°–49° C. for about 3 hours. Heating and phosgene addition were discontinued and stirring of the reaction mixture under nitrogen continued for about 1 hour before working up. 93.9 g of the desired γ-methyl L-glutamate N-carboxyanhydride was recovered as dense, white crystals, m.p. 97.5°–99° C.

EXAMPLE 8

Tricalcium Phosphate

Tricalcium phosphate (β-whitlockite crystalline form) was prepared by the following technique. A solution of 141.7 grams of calcium nitrate tetrahydrate in 400 ml of water was prepared and the pH adjusted to about pH 11 with concentrated ammonium hydroxide. This solution was then diluted to about 900 ml with water and placed in a three liter flask fitted with a dropping funnel and mechanical stirring apparatus. Separately, 66.1 grams of ammonium phosphate dibasic was added to 750 ml of water. The pH of the resulting solution was adjusted to about pH 11 with concentrated ammonium hydroxide resulting in the formation of a precipitate which was subsequently dissolved by the addition of water (about 2000 ml total volume of the solution). The ammonium phosphate dibasic solution was then slowly added to the reaction flask containing the calcium nitrate tetrahydrate solution and the resulting mixture was stirred overnight. A precipitate formed which was collected by centrifugation, washed with water and again collected by centrifugation. The precipitate was then suspended in a 2 percent aqueous ammonium sulfate solution and filtered leaving a residue which was subsequently dried in vacuo at 90° C. leaving 63.7 g of tricalcium phosphate. The tricalcium phosphate was then sintered at 1150° C. for one hour, and then ground to a fine powder.

EXAMPLE 9

Hydroxyapatite-Poly(γ-Methyl-L-Glutamate) Composite 5.0 g of γ-methyl L-glutamate N-carboxyanhydride was added to 50 ml of a mixture of dioxane-THF (3:1). Upon solubilization, 5.9 g of dry unsintered calcium phosphate tribasic (i.e., hydroxyapatite) was added and the mixture was stirred at room temperature for seven days. The mixture was then poured with stirring into 300 ml of methanol and the product composite was collected by filtration, washed with methanol and dried in vacuo at 80° C. for 6 hours. 9.58 g of a soft, white, homogeneous solid was obtained and subsequently identified as hydroxyapatite-poly(γ-methyl L-glutamate) composite consisting of 61% (by weight) hydroxyapatite. This composite material was easily ground to a fine powder.

EXAMPLE 10

Hydroxyapatite-Poly(γ-Methyl L-Glutamate) Composite

Following a procedure substantially the same as that described in Example 9, 65.2 g of γ-methyl L-glutamate N-carboxyanhydride, 50 g of unsintered hydroxyapatite and 675 ml of a mixture of dioxane-THF (3:1) were stirred continuously for 5 days. Two liters of methanol were then added to the mixture and the desired composite material was recovered as described in Example 9. 98 g of the desired hydroxyapatite-poly(γ-methyl L-glutamate) composite material consisting of 50% (by weight) hydroxyapatite was subsequently recovered.

EXAMPLE 11

Hydroxyapatite-Poly(γ-Benzyl L-Glutamate) Composite 72.6 g of γ-benzyl L-glutamate N-carboxyanhydride, 40 g of unsintered hydroxyapatite, and 700 ml of a mixture of dioxane-THF (3:1) were continuously stirred for four days. The reaction mixture was then poured with stirring into 2500 ml of ethanol and collected by filtration. The residue from the filtration was washed with ethanol, air dried and then dried in vacuo at 60°-70° C. for six hours. 98 g of the desired hydroxyapatite-poly(γ-benzyl L-glutamate) composite material (60 percent by weight hydroxyapatite) was obtained as a white, short fiber-like solid.

EXAMPLE 12

Tricalcium Phosphate-Poly (γ-Benzyl L-Glutamate) Composite

γ-Benzyl L-glutamate N-carboxyanhydride (2.05 g) and sintered tricalcium phosphate (1.14 g) were combined in 40 ml of a mixture of dioxane-THF (3:1) and continuously stirred for 9 days. The resulting composite material was collected by pouring the reaction mixture into 200 ml of ethanol (with stirring) followed by filtration on a fritted glass filter leaving a solid residue. The residue was washed with ethanol and dried in vacuo to give 2.73 g of the desired tricalcium phosphate-poly(γ-benzyl L-glutamate) composite material (60 percent by weight tricalcium phosphate).

EXAMPLE 13

Tricalcium Phosphate-Poly (γ-Methyl L-Glutamate) Composite

γ-Methyl L-glutamate N-carboxyanhydride (129.3 g) was dissolved in 1600 ml of a mixture of dioxane-THF (3:1). While maintaining a positive nitrogen flow through the system, 98.9 g of sintered tricalcium phosphate was added and the resulting mixture was continuously stirred for 12 days. The composite material thus formed was collected by pouring the reaction mixture into about 1500 ml of methanol followed by filtration on a fritted glass filter leaving a solid residue. The residue was washed with three 500 ml portions of methanol and then dried in vacuo at 70° C. for 20 hours to give 194.2 g of the desired tricalcium phosphate-poly(γ-methyl L-glutamate) composite material (50 percent by weight tricalcium phosphate) as a soft, white, powdery material.

EXAMPLE 14

A hydroxyapatite-poly(γ-benzyl L-glutamate) composite was ground and sieved through a 20-mesh screen. PEOX (molecular weight about 200,000) was ground and sieved through a 35-mesh screen. Enough PEOX was added to the ground composite to constitute about 15 percent by weight of the total mixture (i.e., composite plus PEOX) and the mixture was blended by tumbling on a roller for 2 hours. This mixture was then compression molded in nickel plated stainless steel pressurized dies held in a ram press under a 2.5 ton load at 160° C. One die was cylindrical in shape and produced a pressure of about 25,500 pounds per square inch (psi) at the composite surface. Another die was dogbone shaped, producing a pressure of about 2600 psi at the composite surface. Molding time was 20 minutes, with about 10 minutes additional being allowed for the preheated press and die to approach the desired molding temperature. About 3-3.5 g of the composite-PEOX mixture was used to produce a molded, 0.5 inch disc in the cylindrical die. Similarly, about 7-7.5 g of the composite-PEOX mixture was used to produce 0.125 inch thick bars in the dogbone shaped die. The molded products were white, smooth, homogeneous objects.

EXAMPLE 15

The same procedure used in Example 14 was repeated utilizing a hydroxyapatite-poly(γ-methyl L-glutamate) composite and PEOX mixture. The mixture was molded in the dies described above under 2.5 ton load at 220° C. The molded products were white, smooth, homogeneous objects.

EXAMPLE 16

Tricalcium phosphate-poly(γ-methyl L-glutamate) composite material was ground and sieved through a 35 mesh screen. Enough sodium chloride was added to the ground composite to constitute 15 percent by weight of the total mixture (i.e., composite plus sodium chloride). The mixture was blended by tumbling on a roller overnight and was subsequently molded as described in Example 15.

Similarly, tricalcium phosphate-poly(γ-benzyl L-glutamate) composite material was admixed with a sufficient quantity of sodium chloride to constitute 15 percent sodium chloride by weight of the total mixture (i.e., composite plus sodium chloride). The mixture was blended and then molded as described in Example 14.

EXAMPLE 17

The same procedures utilized in Examples 14 and 15 were again repeated using sodium chloride in place of PEOX as the pore-forming agent. Again, the resulting molded products were white, smooth, homogeneous objects.

EXAMPLE 18

In order to illustrate the porositization technique, a 2.934 g molded disc containing 87 percent hydroxyapatite-poly(γ-methyl L-glutamate) composite material (50 percent by weight of each constituent) and 13 percent PEOX blended therein was placed in 20 ml of water in a closed container for a total of six days (the water was changed after four days). The disc was removed and dried by blotting with absorbent paper and then further dried in an oven at 60° C. 0.325 g of weight was lost representing 85.3 percent of the available PEOX in the molded disc. Microscopy of a section of the porositized product showed pore sizes of 10–25 microns.

Utilizing the above procedure, a molded disc containing 85 percent hydroxyapatite-poly(γ-methyl L-glutamate) composite (50 percent by weight of each component) and 15 percent by weight sodium chloride blended therein was placed in water in a closed container (48 percent of the available sodium chloride was removed). Microscopy of a section of the disc showed varied pore sizes, some in excess of 100 microns.

Similarly, a molded bar weighing 9.92 g containing 85 percent by weight tricalcium phosphate-poly-(γ-methyl L-glutamate) composite (50 percent by weight of each constituent) blended with 15 percent by weight sodium chloride was placed in 250 ml of water in a closed container. After 10 days, the bar was removed, dried in vacuo for 7 hours at 90° C. and weighed. 77.3 percent (1.15 g) of the available sodium chloride had been removed.

The process of the present invention can be used to prepare composites such as those described herein having desirable properties. Utilizing procedures described herein, additional composite materials set forth in Table 1 were prepared. Table 2 describes the mechanical properties of various molded composite materials.

TABLE 1

| | Composite Material | | | |
|---|---|---|---|---|
| | | Calcium Phosphate | Porositization Mode | |
| Example No. | Polymer[a] | Biomaterial[b] (Weight %) | Agent (Amount)[c] | Amount Removed[d] |
| 19 | PGMLG | HA (50) | None | — |
| 20 | PGMLG | HA (50) | None | — |
| 21 | PGMLG | HA (50) | PEOX (15) | 80 |
| 22 | PGMLG | HA (50) | PEOX (15) | 122[e] |
| 23 | PGMLG | HA (50) | NaCl (15) | 48 |
| 24 | PGBLG | HA (40) | None | — |
| 25 | PGBLG | HA (40) | None | — |
| 26 | PGBLG | HA (40) | PEOX (15) | 29 |
| 27 | PGBLG | HA (40) | PEOX (15) | 59 |
| 28 | PGMLG | TCP (50) | NaCl (15) | 63 |
| 29 | PGMLG | TCP (50) | None | — |
| 30 | PGMLG | TCP (50) | NaCl (15) | 65 |
| 31 | PGMLG | TCP (50) | None | — |
| 32 | PGMLG | HA (50) | NaCl (10) | 55 |
| 33 | PGMLG | HA (50) | NaCl (20) | 40 |
| 34 | PGMLG | HA (75) | NaCl (15) | 78 |

[a]Abbreviations:
PGMLG = poly(γ-methyl L-glutamate)
PGBLG = poly(γ-benzyl L-glutamate)
[b]Abbreviations:
HA = hydroxyapatite
TCP = tricalcium phosphate
[c]Weight percent of the porositizing agent based on the total weight of the composite material plus porositizing agent.
[d]Refers to the percent by weight of porositizing agent removed (based on the theoretical amount of porositizing agent available) by leaching with water.
[e]Result due to error in weighing.

TABLE 2

MECHANICAL PROPERTIES OF VARIOUS COMPOSITE MATERIALS

| | | Compression Data | | | |
|---|---|---|---|---|---|
| Composite of Example No. | Vicat Heat Distortion | Strength (psi) | Deformation (%) | Recovery[a] (%) | Modulus (psi × $10^5$) |
| 19 | — | 12,380 | 0.20 | — | 4.28 |
| 20 | 230° C. | — | — | — | — |
| 21 | — | 5,177 | — | — | — |
| 22 | 230° C. | — | — | — | — |
| 23 | — | 9,029 | 3.6 | 27.8 | 3.75 |
| 24 | — | 3,809 | 1.25 | 42.4 | 1.78 |
| 25 | 99° C. | — | — | — | — |
| 26 | — | 3,542 | — | — | — |
| 27 | 91° C. | — | — | — | — |
| 28 | — | 4,824 | — | — | 3.13 |
| 29 | — | 8,034 | 3.61 | 31.8 | 3.77 |
| 34 | — | 8,017 | 1.26 | 20.0 | 4.30 |

[a]After 24 hours.

EXAMPLE 35

Molded discs containing 85 percent hydroxyapatite-poly(γ-methyl L-glutamate) composite (50 percent by weight of each component) and 15 percent sodium chloride blended therein (hereafter referred to as the 15 percent NaCl composite discs) were porositized by the general techniques described herein. Similarly, molded discs containing 80 percent hydroxyapatite-poly(γ-methyl L-glutamate) composite (50 percent by weight of each component) and 20 percent sodium chloride blended therein (hereafter referred to as the 20 percent NaCl composite discs) were also prepared and porositized for evaluation in the study described below.

Small pieces of the above-described molded composites were cut from the larger discs with a diamond blade and subsequently autoclaved for sterilization. The sterilized pieces were then surgically implanted into rabbits in an incision in the paravertebral muscles of the lumbar region and in a hole drilled in the iliac crest. X-rays taken 6 and 12 weeks later of the rabbits implanted with the 15 percent NaCl composite discs showed no remarkable soft-tissue response in the lumbar paravertebral muscles indicating absence of a chronic inflammatory reaction. The bony implant sites exhibited healing and a regeneration of new bone incorporating the surgically implanted composite material. The animals were sacrificed at 14 weeks and the discs and surrounding musculature of the paravertebral implant were excised for microscopic evaluation. Likewise, iliac crest sections containing the implant sites were surgically removed, decalcified and were subsequently made into paraffin embedded sections. Upon examination, the discs showed a thin, fibrous encapsulation of from about 10 to about 50 microns evidencing only a minor foreign body response.

Animals implanted with the 20 percent NaCl composite discs showed a similar clinical history except that eight weeks after implantation there was no fibrous capsule formation around the implants and marrow was observed growing into the pores of the discs.

What is claimed is:

1. A process for the preparation of a composite material containing from about 25 to about 75 percent by weight of a calcium phosphate biomaterial and about 75 to about 25 percent by weight of an α-amino acid polymer which comprises polymerizing in situ an N-carboxyanhydride of an α-amino acid in the presence of a powdered calcium phosphate biomaterial, said polymerization taking place in an inert organic solvent.

2. A process for the preparation of a composite material containing from about 40 to about 60 percent by weight of a calcium phosphate biomaterial and from about 60 to about 40 percent by weight of an α-amino acid polymer which comprises polymerizing in situ an N-carboxyanhydride of an α-amino acid in the presence of a powdered calcium phosphate biomaterial, said polymerization taking place in an inert organic solvent.

3. The process of claim 1 wherein said N-carboxyanhydride is glutamic acid N-carboxyanhydride and said calcium phosphate biomaterial is hydroxyapatite, tricalcium phosphate, or mixtures thereof.

4. The process of claim 2 wherein said N-carboxyanhydride is glutamic acid N-carboxyanhydride and said calcium phosphate biomaterial is hydroxyapatite, tricalcium phosphate, or mixtures thereof.

5. The process of claim 3 wherein said glutamic acid N-carboxyanhydride has a γ-ester residue.

6. The process of claim 4 wherein said glutamic acid N-carboxyanhydride has a γ-ester residue.

7. The process of claim 5 wherein said γ-ester residue is a methyl or benzyl ester of glutamic acid.

8. The process of claim 6 wherein said γ-ester residue is a methyl or benzyl ester of glutamic acid.

9. The process of claim 1 carried out at ambient temperature and pressure.

10. The process of claim 2 carried out at ambient temperature and pressure.

11. The process of claim 1 wherein said inert organic solvent is selected from the group consisting of chloroform, dioxane, tetrahydrofuran, methylene chloride, and mixtures thereof.

12. The process of claim 2 wherein said inert organic solvent is selected from the group consisting of chloroform, dioxane, tetrahydrofuran, methylene chloride, and mixtures thereof.

* * * * *